United States Patent [19]
Yoshioka et al.

[11] Patent Number: 5,143,930
[45] Date of Patent: Sep. 1, 1992

[54] THIAZOLIDINE DERIVATIVES WITH ANTI-DIABETIC ACTIVITY, THEIR PREPARATION AND THEIR USE

[75] Inventors: Takao Yoshioka; Takashi Fujita; Tsutomu Kanai; Kanichi Nakamura; Hiroyoshi Horikoshi; Kunihiro Sasahara; Takeshi Kinoshita, all of Tokyo, Japan

[73] Assignee: Sankyo Company, Limited, Tokyo, Japan

[21] Appl. No.: 645,108

[22] Filed: Jan. 24, 1991

[30] Foreign Application Priority Data

Feb. 7, 1990 [JP] Japan .................... 2-28023

[51] Int. Cl.$^5$ .................. C07D 417/12; A01K 31/425
[52] U.S. Cl. ..................... 514/369; 548/183
[58] Field of Search .................. 588/183; 514/369

[56] References Cited

U.S. PATENT DOCUMENTS

| | | | |
|---|---|---|---|
| 4,572,912 | 2/1986 | Yoshioka et al. | 548/183 |
| 4,873,255 | 11/1989 | Yoshioka et al. | 548/183 |
| 4,933,355 | 6/1990 | Yoshioka et al. | 548/183 |

*Primary Examiner*—Robert Gerstl
*Attorney, Agent, or Firm*—Frishauf, Holtz, Goodman & Woodward

[57] ABSTRACT

Compounds of formula (I):

$$A-W-U-\underset{\underset{OH}{|}}{\overset{\overset{R^1}{|}}{C}}-(CH_2)_n-O-C\underset{HC-CH}{\overset{HC=CH}{\diagup\diagdown}}C-CH_2-CH\underset{S\diagdown_{C}\diagup NH}{\overset{\diagup C\diagdown O}{|}}$$
$$\phantom{AAAAAAAAAAAAAAAAAAAAAAAAAAAAAAAAAAAAAAAA}\overset{\|}{O}$$

in which: A is a group of formula (II) or (III):

$$\underset{Y^1O}{\overset{R^4}{\diagdown}}\underset{C=C}{\overset{C-C}{\diagup\diagdown}}\underset{R^2}{\overset{OY^2}{\diagup}}C- \quad \text{or} \quad R^3-\underset{O}{\overset{R^4}{\diagdown}}\underset{C-C}{\overset{C-C}{\diagup\diagdown}}\underset{R^2}{\overset{O}{\diagup}}C-$$

(II) \qquad\qquad (III)

W is methylene, carbonyl or $>C=N-OV$, where V is hydrogen, sulfo, acyl or alkyl; U is methylene, or W is absent and U is a carbon-carbon double bond between A and $-CR^1(OH)-$; $R^1$, $R^2$, $R^3$ and $R^4$ are each hydrogen or alkyl; $Y^1$ and $Y^2$ are each hydrogen or a hydroxy-protecting group; and n is 1, 2 or 3 and salts thereof have anti-diabetic activity in mammals. Methods of preparing them are also provided.

34 Claims, No Drawings

THIAZOLIDINE DERIVATIVES WITH ANTI-DIABETIC ACTIVITY, THEIR PREPARATION AND THEIR USE

BACKGROUND TO THE INVENTION

The present invention relates to a series of new thiazolidine derivatives, which exhibit anti-diabetic activity in mammals, and provides methods and compositions using them, as well as processes for their preparation.

Thiazolidine derivatives which can reduce blood sugar levels have been described, for example, in Japanese Patent Application Kokai No. Sho 55-22636 (Tokko No. Sho 62-42903), European Patent Publications No. 139 421 and 207 581, Japanese Patent Application Kokai No. Sho 61-36284 and No. Sho 62-5980 and Y. Kawamatsu et al., Chem. Pharm. Bull., 30, 3580–3600 (1982). These prior compounds all differ structurally from the compounds of the present invention.

We have now discovered a series of new thiazolidine derivatives, which have a particularly good activity, in some cases much better than the prior compounds referred to above. In particular, the compounds of the present invention show a significant ability to suppress hepatic gluconeogenesis, which ability is expected to result in a level of reduction in fasting blood sugar levels which is substantially better than is achieved by the compounds disclosed in the prior art referred to above.

BRIEF SUMMARY OF INVENTION

It is, therefore, an object of the present invention to provide a series of new thiazolidine derivatives, which have the ability to reduce diabetic complications and which can, therefore, be used in the treatment and prophylaxis of various diseases and disorders arising from high blood sugar levels, for example hyperlipemia, diabetes and their complications.

The compounds of the present invention are those compounds of formula (I):

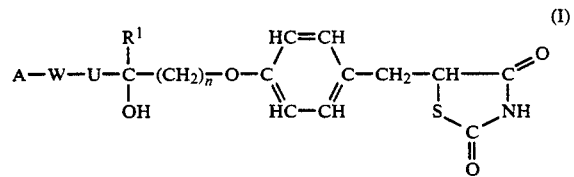

(I)

in which:

A represents a group of formula (II) or (III):

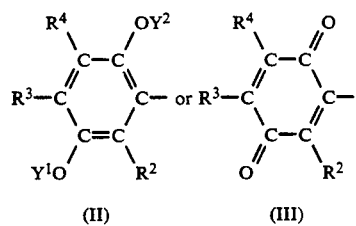

(II)           (III)

W represents a methylene group ($>CH_2$), a carbonyl group ($>C=O$) or a group of formula $>C=N-OV$ in which V represents a hydrogen atom, a sulfo group, an acyl group as defined below or an alkyl group which has from 1 to 8 carbon atoms and which is unsubstituted or has at least one substituent selected from the group consisting of substituents (a), defined below;

U represents a methylene group; or W is absent and U represents a carbon-carbon double bond between the group represented by A and the group $-CR^1(OH)-$;

$R^1$ represents a hydrogen atom or an alkyl group having from 1 to 8 carbon atoms;

$R^2$ and $R^4$ are independently selected from the group consisting of hydrogen atoms and alkyl groups having from 1 to 8 carbon atoms;

$R^3$ represents a hydrogen atom or an alkyl group having from 1 to 10 carbon atoms;

$Y^1$ and $Y^2$ are independently selected from the group consisting of hydrogen atoms and hydroxy-protecting groups, said hydroxy-protecting groups being preferably: aliphatic acyl groups having from 1 to 25 carbon atoms; halogenated alkanoyl groups having from 2 to 6 carbon atoms; alkoxyalkanoyl groups in which the alkoxy part has from 1 to 5 carbon atoms and the alkanoyl part has from 2 to 6 carbon atoms; alkenoyl or alkynoyl groups having from 3 to 6 carbon atoms; aromatic acyl groups in which the aryl part has from 6 to 14 ring carbon atoms and is a carbocyclic group, which is unsubstituted or has from 1 to 5 substituents selected from the group consisting of substituents (c), defined below; heterocyclic groups having 5 or 6 ring atoms, of which 1 or 2 are hetero-atoms selected from the group consisting of oxygen, sulfur and nitrogen atoms, which groups may be unsubstituted or may have at least one substituent selected from the group consisting of substituents (c), defined below, and oxygen atoms; tri-substituted silyl groups, in which all three or two or one of the substituents are alkyl groups having from 1 to 5 carbon atoms, and none, one or two of the substituents are aryl groups, as defined above; alkoxyalkyl groups, in which the alkoxy and alkyl parts each have from 1 to 5 carbon atoms; alkoxy-substituted alkoxymethyl groups in which each alkoxy part has from 1 to 5 carbon atoms; halogenated alkoxymethyl groups in which the alkoxy part has from 1 to 5 carbon atoms; halogenated ethyl groups; arylselenyl-substituted ethyl groups, in which the aryl part is as defined above; aralkyl groups in which the alkyl part has from 1 to 5 carbon atoms and the aryl part is a carbocyclic aryl group which has from 6 to 14 ring carbon atoms and which may be unsubstituted or substituted on the aryl part with an alkyl group, an alkoxy group, a nitro group, a halogen atom, a cyano group, or an alkylenedioxy group having from 1 to 3 carbon atoms; alkoxycarbonyl groups which have from 2 to 7 carbon atoms and which are unsubstituted or substituted with a halogen atom or a tri-substituted silyl group, as defined above; alkenyloxycarbonyl groups in which the alkenyl part has from 2 to 6 carbon atoms; sulfo groups; and aralkyloxycarbonyl groups, in which the aralkyl part is as defined above;

n is 1, 2 or 3;

said acyl group included in the definition of V is: an unsubstituted aliphatic acyl group which contains from 1 to 6 carbon atoms; a substituted aliphatic acyl group which contains from 2 to 6 carbon atoms and which is substituted with at least one substituent selected from the group consisting of substituents (b), defined below; an aromatic acyl group in which the aryl part is a carbocyclic aromatic ring which has from 6 to 14 ring carbon atoms and which is unsubstituted or has at least one substituent selected from the group consisting of substituents (c), defined below; or a heterocyclic acyl group having a heterocyclic ring containing 5 or 6 ring atoms, of which 1, 2 or 3 are hetero-atoms selected from the group consisting of nitrogen, oxygen and sulfur atoms, the heterocyclic ring being unsubstituted or having at least one substituent selected from the group consisting of substituents (c), defined below, and oxygen atoms;

said substituents (a) are selected from the group consisting of alkoxycarbonyl groups having from 2 to 6 atoms, carboxy groups and carbocyclic aryl groups which have from 6 to 10 ring carbon atoms and which are unsubstituted or have at least one substituent selected from the group consisting of substituents (c), defined below;

said substituents (b) are selected from the group consisting of halogen atoms and alkoxy groups having from 1 to 5 carbon atoms;

said substituents (c) are selected from the group consisting of alkyl groups having from 1 to 5 carbon atoms, alkoxy groups having from 1 to 5 carbon atoms, halogen atoms, halogenated alkyl groups having from 1 to 3 carbon atoms, nitro groups, hydroxy groups, alkoxycarbonyl groups having from 2 to 6 carbon atoms and aryl groups which have from 6 to 10 ring carbon atoms and which are unsubstituted or have at least one substituent selected from the group consisting of substituents (d), defined below; and said substituents (d) are selected from the group consisting of alkyl groups having from 1 to 5 carbon atoms, alkoxy groups having from 1 to 5 carbon atoms, halogen atoms, halogenated alkyl groups having from 1 to 3 carbon atoms, nitro groups and hydroxy groups;

and salts thereof.

The invention also provides a pharmaceutical composition for the treatment or prophylaxis of diabetes or hyperlipemia, which comprises an effective amount of an active compound in admixture with a pharmaceutically acceptable carrier or diluent, wherein said active compound is selected from the group consisting of compounds of formula (I), defined above, and pharmaceutically acceptable salts thereof.

The invention still further provides a method for the treatment or prophylaxis of diabetes or hyperlipemia in a mammal, which may be human, which method comprises administering to said mammal an effective amount of an active compound, wherein said active compound is selected from the group consisting of compounds of formula (I), defined above, and pharmaceutically acceptable salts thereof.

The invention also provides processes for the preparation of the compounds of the present invention, which processes are described in more detail hereafter.

DETAILED DESCRIPTION OF INVENTION

Where substituents are referred to in general terms herein, without specifying the number thereof, there is, in principle, no limitation upon their number, except such as may be dictated by the number of substitutable positions, and possibly by steric constraints. However, in general, it may be said that from 1 to 5 such substituents are preferred, from 1 to 3 being more preferred, and 1 normally being most preferred.

In the compounds of the invention, where $R^1$ represents an alkyl group, this may be a straight or branched chain alkyl group having from 1 to 8 carbon atoms, preferably from 1 to 4 carbon atoms. Examples of such alkyl groups include the methyl, ethyl, propyl, isopropyl, butyl, isobutyl, sec-butyl, pentyl, isopentyl, hexyl, 1,3-dimethylbutyl, heptyl, octyl, 1-methylheptyl and 2-ethylhexyl groups. Of these, the methyl, ethyl and isobutyl groups are more preferred and the methyl group is most preferred.

Where $R^3$ represents an alkyl group, this may be a straight or branched chain alkyl group having 1 to 10 carbon atoms, preferably from 1 to 8 carbon atoms, more preferably from 1 to 4 carbon atoms. Examples of such alkyl groups include the methyl, ethyl, propyl, isopropyl, butyl, isobutyl, sec-butyl, t-butyl, pentyl, isopentyl, neopentyl, hexyl, 1,1-dimethylbutyl, 1,3-dimethylbutyl, heptyl, octyl, 1-methylheptyl, 2-ethylhexyl, 1,1,3,3-tetramethylbutyl, nonyl and decyl groups. Of these, the methyl and t-butyl groups are more preferred, the methyl group being most preferred.

Where $R^2$ or $R^4$ represents an alkyl group, this may be a straight or branched chain alkyl group having from 1 to 8 carbon atoms, preferably from 1 to 3 carbon atoms. Examples of such alkyl groups include the methyl, ethyl, propyl, isopropyl, butyl, isobutyl, sec-butyl, pentyl, isopentyl, hexyl, 1,3-dimethylbutyl, heptyl, octyl, 1-methylheptyl and 2-ethylhexyl groups. Of these, the methyl group is most preferred.

Where V represents an alkyl group, it may be a straight or branched chain alkyl group having from 1 to 8 carbon atoms, preferably from 1 to 4 carbon atoms, and may optionally have substituents, preferably selected from the group consisting of substituents (a), defined above and exemplified below. Examples of such unsubstituted groups include the methyl, ethyl, propyl, isopropyl, butyl, isobutyl, sec-butyl, pentyl, isopentyl, hexyl, 1,3-dimethylbutyl, heptyl, octyl, 1-methylheptyl and 2-ethylhexyl groups. Where the group is substituted, it preferably has from 1 to 5 substituents (depending upon the availability of substitutable positions) selected from the group consisting of substituents (a), i.e.:

carbocyclic aryl groups which have from 6 to 10 ring carbon atoms, preferably 6 or 10, and most preferably 6, ring carbon atoms, and which may optionally be substituted by at least one substituent selected from the group consisting of alkyl groups having from 1 to 5 carbon atoms (e.g. the methyl, ethyl, propyl, isopropyl, butyl, isobutyl, sec-butyl, t-butyl, pentyl or isopentyl groups), halogen atoms (e.g. the chlorine, fluorine, bromine or iodine atoms) and alkoxy groups having from 1 to 5 carbon atoms (e.g. the methoxy, ethoxy, propoxy, isopropoxy, butoxy, isobutoxy, sec-butoxy, t-butoxy or pentyloxy groups); examples of such substituted and unsubstituted groups include the phenyl, p-methylphenyl, m-chlorophenyl and o-methoxyphenyl groups;

the carboxy group; and alkoxycarbonyl groups having from 2 to 6 carbon atoms, such as the ethoxycarbonyl and t-butoxycarbonyl groups.

The preferred substituents (a) are the alkoxy-carbonyl groups having from 2 to 6 carbon atoms and the carboxy group, the carboxy group being most preferred.

Of these substituted and unsubstituted alkyl groups, the methyl, alkoxycarbonylmethyl and carboxymethyl groups are the more preferred, the carboxymethyl group being most preferred.

Where V represents an acyl group, it may be a straight or branched chain aliphatic acyl group containing from 1 to 6 carbon atoms, if unsubstituted, or from 2 to 6 carbon atoms, if substituted; and it preferably has from 2 to 6 carbon atoms in any event, more preferably from 2 to 4 carbon atoms. Examples of such groups include the acetyl, propionyl, butyryl and hexanoyl groups. Of these, the acetyl group is most preferred. Such a group may be, and preferably is, unsubstituted, or it may be substituted by at least one substituent selected from the group consisting of substituents (b), defined above and exemplified below, i.e. halogen atoms or alkoxy groups having from 1 to 5 carbon atoms.

Examples of the groups and atoms which may be included in substituents (b) are:
    halogen atoms, such as the chlorine, fluorine, bromine and iodine atoms; and
    alkoxy groups having from 1 to 5 carbon atoms, such as the methoxy, ethoxy, propoxy, isopropoxy, butoxy, isobutoxy, sec-butoxy, t-butoxy and pentyloxy groups.

Alternatively, where V represents an aromatic acyl group, the aromatic part of this is a carbocyclic aryl group which has from 6 to 14, preferably from 6 to 10, more preferably 6 or 10 and most preferably 6, ring carbon atoms and which is unsubstituted or has at least one substituent selected from the group consisting of substituents (c), defined above and exemplified below. Examples of such substituted and unsubstituted groups include the benzoyl, naphthoyl (1- or 2- naphthoyl), 3-methylbenzoyl, 2,4-dimethylbenzoyl, 4-ethylbenzoyl, 4-butylbenzoyl, p-anisoyl, 4-ethoxybenzoyl, 4-butoxybenzoyl, 3-chlorobenzoyl, 2-bromobenzoyl, 4-fluorobenzoyl, 4-trifluoromethylbenzoyl, 3-nitrobenzoyl, 2,4-dinitrobenzoyl, salicyloyl and 4-hydroxybenzoyl groups.

Alternatively, where V represents a heterocyclic acyl group, this has 5 or 6 ring atoms, of which 1, 2 or 3 are hetero-atoms selected from the group consisting of nitrogen, oxygen and sulfur atoms, the heterocyclic ring being unsubstituted or having at least one substituent selected from the group consisting of substituents (c), defined above and exemplified below, and oxygen atoms. Where the heterocyclic ring has three hetero-atoms, we prefer that all three should be nitrogen atoms, or that one or two (preferably two) should be nitrogen atoms, and correspondingly two or one should be oxygen or sulfur atoms. Where the heterocyclic ring has two hetero-atoms, these are preferably different or both are nitrogen atoms, more preferably one of the hetero-atoms is a nitrogen atom and the other is selected from the group consisting of nitrogen, oxygen and sulfur atoms, still more preferably nitrogen and oxygen atoms. Examples of such groups include the 2-thenoyl, 3-furoyl, picolinoyl, 2-pyridinecarbonyl, nicotinoyl, isonicotinoyl, 4-isoxazolecarbonyl, 1-(1,2,3-triazolyl)-carbonyl, 2-, 3- or 4- piperidinylcarbonyl and 1-pyrrolidinylcarbonyl groups. Such groups may be, and preferably are, unsubstituted, or they may have one or more substituents selected from the group consisting of substituents (c), defined above and exemplified below. Where the group is substituted, the number of substituents is preferably from 1 to 5 (depending on the availability of substitutable positions), more preferably from 1 to 3, and most preferably 1.

In general, the preferred groups and atoms represented by V are: a hydrogen atom; a sulfo group; an unsubstituted alkyl group having from 1 to 4 carbon atoms; a substituted alkyl group having from 1 to 4 carbon atoms in which the substituents are selected from the group consisting of aryl groups which have from 6 to 10 ring carbon atoms and which are unsubstituted or are substituted by at least one alkyl substituent having from 1 to 5 carbon atoms, carboxy groups and alkoxycarbonyl groups having from 2 to 6 carbon atoms; an aliphatic carboxylic acyl group having from 1 to 6 carbon atoms; or a carbocyclic aromatic carboxylic acyl group in which the aryl part has 6 or 10 ring carbon atoms, said group being unsubstituted or having at least one substituent selected from the group consisting of substituents (c), defined in Claim 1.

Examples of groups and atoms which may be included in substituents (c) are:
    alkyl groups having from 1 to 5 carbon atoms, such as the methyl, ethyl, propyl, isopropyl, butyl, isobutyl, sec-butyl, t-butyl, pentyl and isopentyl groups;
    alkoxy groups having from 1 to 5 carbon atoms, such as the methoxy, ethoxy, propoxy, isopropoxy, butoxy, isobutoxy, sec-butoxy, t-butoxy, pentyloxy and isopentyloxy groups;
    halogen atoms, such as those illustrated above in relation to substituents (b);
    halogenated alkyl groups having from 1 to 3 carbon atoms, such as the chloromethyl, fluoromethyl, bromomethyl, iodomethyl, dichloromethyl, difluoromethyl, dibromomethyl, diiodomethyl, trichloromethyl, trifluoromethyl, tribromomethyl, triiodomethyl, 2-chloroethyl, 2-fluoroethyl, 2-bromoethyl, 2-iodoethyl, 2,2-dichloroethyl, 2,2-difluoroethyl, 2,2-dibromoethyl, 2,2-diiodoethyl, 2,2,2-trichloroethyl, 2,2,2-trifluoroethyl, 2,2,2-tribromoethyl and 2,2,2-triiodoethyl groups;
    nitro groups and hydroxy groups;
    alkoxycarbonyl groups having from 2 to 6 carbon atoms, as exemplified in relation to substituents (a); and
    aryl groups which are unsubstituted or have at least one substituent selected from the group consisting of substituents (d), defined below, as exemplified in relation to substituents (a).

Where one or both of $Y^1$ and $Y^2$ represents a hydroxy-protecting group, there is no particular limitation on the nature of the protecting group, provided that it can act as a protecting group in the reaction for the preparation of the compound or in another reaction to which the compound is to be subjected, and that, where the compound is to be used therapeutically, it can readily be hydrolyzed in vivo and used as a pro-druq at the time of administration. Where the compound is to be used for non-therapeutic purposes, e.g. as an intermediate in the preparation of another compound, it is, of course, unnecessary that the protecting group should be selected with this requirement in mind, and it can be selected solely on the basis of its utility as a protecting group in the reaction. Examples of such protecting groups include:
    aliphatic acyl groups, preferably: alkanoyl groups having from 1 to 25 carbon atoms, more preferably from 1 to 20 carbon atoms, still more preferably from 1 to 6 carbon atoms, and most preferably from 1 to 4 carbon atoms, (such as the formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups, of which the acetyl group is most preferred); halogenated alkanoyl groups having from 2 to 6 carbon atoms, especially halogenated acetyl groups (such as the chloroacetyl, dichloroacetyl, trichloroacetyl and trifluoroacetyl groups); lower alkoxyalkanoyl groups in which the alkoxy part has from 1 to 5, preferably from 1 to 3, carbon atoms and the alkanoyl part has from 2 to 6 carbon atoms and is preferably an acetyl group (such as the methoxyacetyl group); and unsaturated analogs of such groups, especially alkenoyl or alkynoyl groups having from 3 to 6 carbon atoms [such as the acryloyl, methacryloyl, propioloyl, crotonoyl, isocrotonoyl and (E)-2-methyl-2-butenoyl groups];

aromatic acyl groups, preferably arylcarbonyl groups, in which the aryl part has from 6 to 14, more preferably from 6 to 10, still more preferably 6 or 10, and most preferably 6, ring carbon atoms and is a carbocyclic group, which is unsubstituted or has from 1 to 5, preferably from 1 to 3 substituents, selected from the group consisting of substituents (c), defined above and exemplified below, preferably: unsubstituted groups (such as the benzoyl, α-naphthoyl and β-naphthoyl groups); halogenated arylcarbonyl groups (such as the 2-bromobenzoyl and 4-chlorobenzoyl groups); lower alkyl-substituted arylcarbonyl groups, in which the or each alkyl substituent has from 1 to 5, preferably from 1 to 4, carbon atoms (such as the 2,4,6-trimethylbenzoyl and 4-toluoyl groups); lower alkoxy-substituted arylcarbonyl groups, in which the or each alkoxy substituent preferably has from 1 to 5, preferably from 1 to 4, carbon atoms (such as the 4-anisoyl group); nitro-substituted arylcarbonyl groups (such as the 4-nitrobenzoyl and 2-nitrobenzoyl groups); lower alkoxycarbonyl-substituted arylcarbonyl groups, in which the or each alkoxycarbonyl substituent preferably has from 2 to 6 carbon atoms [such as the 2-(methoxycarbonyl)-benzoyl group]; and aryl-substituted arylcarbonyl groups, in which the aryl substituent is as defined above, except that, if it is substituted by a further aryl group, that aryl group is not itself substituted by an aryl group (such as the 4-phenylbenzoyl group);

heterocyclic groups having 5 or 6 ring atoms, of which 1 or 2 are hetero-atoms selected from the group consisting of oxygen, sulfur and nitrogen atoms, preferably oxygen or sulfur atoms, which groups may be unsubstituted or may have at least one substituent selected from the group consisting of substituents (c), defined and exemplified above, and oxygen atoms; the preferred heterocyclic groups have fully saturated ring systems; examples include: the tetrahydropyranyl groups, which may be substituted or unsubstituted, such as the tetrahydropyran-2-yl, 3-bromotetrahydropyran-2-yl and 4-methoxytetrahydropyran-4-yl groups; tetrahydrothiopyranyl groups, which may be substituted or unsubstituted, such as the tetrahydrothiopyran-2-yl and 4-methoxytetrahydrothiopyran-4-yl groups; tetrahydrofuranyl groups, which may be substituted or unsubstituted, such as the tetrahydrofuran-2-yl group; and tetrahydrothienyl groups, which may be substituted or unsubstituted, such as the tetrahydrothien-2-yl group;

tri-substituted silyl groups, in which all three or two or one of the substituents are alkyl groups having from 1 to 5, preferably from 1 to 4, carbon atoms, and correspondingly none, one or two of the substituents are aryl groups, as defined above, but preferably phenyl or substituted phenyl groups, preferably: tri(lower alkyl)silyl groups (such as the trimethylsilyl, triethylsilyl, isopropyldimethylsilyl, t-butyldimethylsilyl, methyldiisopropylsilyl, methyldi-t-butylsilyl and triisopropylsilyl groups); and tri(lower alkyl)silyl groups in which one or two of the alkyl groups have been replaced by aryl groups (such as the diphenylmethylsilyl, diphenylbutylsilyl, diphenyl-t-butylsilyl, diphenylisopropylsilyl and phenyldiisopropylsilyl groups);

alkoxyalkyl groups, in which the alkoxy and alkyl parts each have from 1 to 5, preferably from 1 to 4, carbon atoms, especially alkoxymethyl groups, and such groups which have at least one, preferably from 1 to 5, more preferably from 1 to 3, and most preferably 1, substituents, preferably: lower alkoxymethyl groups and other alkoxyalkyl groups (such as the methoxymethyl, 1,1-dimethyl-1-methoxymethyl, ethoxymethyl, propoxymethyl, isopropoxymethyl, butoxymethyl and t-butoxymethyl groups); lower alkoxy-substituted lower alkoxymethyl groups (such as the 2-methoxyethoxymethyl group); halogenated lower alkoxymethyl groups [such as the 2,2,2-trichloroethoxymethyl and bis(2-chloroethoxy)-methyl groups] and lower alkoxy-substituted ethyl groups (such as the 1-ethoxyethyl, 1-methyl-1-methoxyethyl and 1-isopropoxyethyl groups); other substituted ethyl groups, preferably: halogenated ethyl groups (such as the 2,2,2-trichloroethyl group); and arylselenyl-substituted ethyl groups, in which the aryl part is as defined above [such as the 2-(phenylselenyl)ethyl group];

aralkyl groups, preferably alkyl groups having from 1 to 4, more preferably from 1 to 3 and most preferably 1 or 2, carbon atoms which are substituted with from 1 to 3 aryl groups, as defined and exemplified above, which may be unsubstituted (such as the benzyl, phenethyl, 1-phenylethyl, 3-phenylpropyl, α-naphthylmethyl, β-naphthylmethyl, diphenylmethyl, triphenylmethyl, α-naphthyldiphenylmethyl and 9-anthrylmethyl groups) or substituted on the aryl part with a lower alkyl group, a lower alkoxy group, a nitro group, a halogen atom, a cyano group, or an alkylenedioxy group having from 1 to 3 carbon atoms, preferably a methylenedioxy group, [such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzoyl, 4-bromobenzyl, 4-cyanobenzyl, 4-cyanobenzyldiphenylmethyl, bis(2-nitrophenyl)methyl and piperonyl groups];

alkoxycarbonyl groups, especially such groups having from 2 to 7, more preferably from 2 to 5, carbon atoms and which may be unsubstituted (such as the methoxycarbonyl, ethoxycarbonyl, t-butoxycarbonyl and isobutoxycarbonyl groups) or substituted with a halogen atom or a tri-substituted silyl group, e.g. a tri(lower alkylsilyl) group (such as the 2,2,2-trichloroethoxycarbonyl and 2-trimethylsilylethoxycarbonyl groups);

alkenyloxycarbonyl groups in which the alkenyl part has from 2 to 6, preferably from 2 to 4, carbon atoms (such as the vinyloxycarbonyl and allyloxycarbonyl groups);

sulfo groups; and aralkyloxycarbonyl groups, in which the aralkyl part is as defined and exemplified above, and in which the aryl ring, if substituted, preferably has one or two lower alkoxy or nitro substituents (such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups).

Of these, we prefer the aliphatic acyl groups having from 1 to 6 carbon atoms, the aromatic acyl groups and the sulfo group; more preferably the aliphatic acyl groups having from 2 to 4 carbon atoms, the unsubstituted aromatic acyl groups and the sulfo group; and most preferably the aliphatic acyl groups having from 2 to 4 carbon atoms, particularly the acetyl group.

Examples of groups and atoms which may be included in substituents (d) are alkyl groups having from 1 to 5 carbon atoms, alkoxy groups having from 1 to 5 carbon atoms, halogen atoms, halogenated alkyl groups having from 1 to 3 carbon atoms, nitro groups and hydroxy groups, all as exemplified in relation to substituents (c).

The compounds of the present invention necessarily contain at least one acidic hydrogen atom (at the 3-position of the thiazolidine ring) and may contain 1 or 2 further acidic hydrogen atoms (when $Y^1$ and/or $Y^2$ represents a hydrogen atom) and the compounds can, therefore, form salts with bases. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. Examples of such salts include: salts with an alkali metal, such as sodium, potassium or lithium; salts with an alkaline earth metal, such as barium or calcium; salts with another metal, such as magnesium or aluminum; organic base salts, such as a salt with dicyclohexylamine; and salts with a basic amino acid, such as lysine or arginine. Where the cation is monovalent, for example, an alkali metal, the compounds of the present invention can form mono-, di- or tri-salts. Pharmaceutically acceptable salts are preferred.

Also, where W represents a group of formula $>C=N-OV$, the resulting compounds may form salts with acids. There is no particular restriction on the nature of these salts, provided that, where they are intended for therapeutic use, they are pharmaceutically acceptable. Where they are intended for non-therapeutic uses, even this restriction does not apply. Examples of such salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid or citric acid; and salts with amino acids, such as glutamic acid or aspartic acid.

The compounds of the present invention contain an asymmetric carbon atom at the 5-position of the thiazolidine ring and, where $R^1$ represents an alkyl group, the carbon atom to which $R^1$ is attached may also be asymmetric. The compounds can, therefore, form stereoisomers. Although these are all represented herein by a single molecular formula, the present invention includes the use of both the individual, isolated isomers and mixtures, including racemates, thereof. Where stereospecific synthesis techniques are employed or optically active compounds are employed as starting materials in the preparation of the compounds, individual isomers may be prepared directly; on the other hand, if a mixture of isomers is prepared, the individual isomers may be obtained by conventional resolution techniques, or the mixture may be used as it is, without resolution.

Furthermore, the thiazolidine part of the compound of formula (I) can exist in the form of the tautomeric isomers shown below, but, in general, all of these tautomers are indicated herein by a single formula (I):

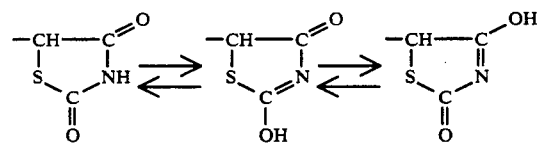

The preferred compounds of the present invention are those compounds of formula (I) and salts thereof in which:

A represents a group of formula (II) or (III), as defined above; W represents a methylene group, a carbonyl group or a group of formula $=C=N-OV$ in which V represents a hydrogen atom, an unsubstituted alkyl group having from 1 to 4 carbon atoms or a substituted alkyl group having from 1 to 4 carbon atoms in which the substituents are selected from the group consisting of aryl groups which have from 6 to 10 ring carbon atoms and which are unsubstituted or are substituted by at least one alkyl substituent having from 1 to 5 carbon atoms, carboxy groups and alkoxycarbonyl groups having from 2 to 6 carbon atoms;

U represents a methylene group;

$R^1$ represents a hydrogen atom or an alkyl group having from 1 to 4 carbon atoms;

$R^2$ and $R^4$ are the same or different and each represents a hydrogen atom or an alkyl group having from 1 to 3 carbon atoms;

$R^3$ represents a hydrogen atom or an alkyl group having from 1 to 4 carbon atoms;

$Y^1$ and $Y^2$ are the same or different and each represents a hydrogen atom, an aliphatic acyl group having from 1 to 6 carbon atoms, an aromatic acyl group, as defined above, or a sulfo group; and n is 1 or 2.

The more preferred compounds of the present invention are those compounds of formula (I) and salts thereof in which:

A represents a group of formula (II) or (III), as defined above;

W represents a methylene group or a group of formula $=C=N-OV$ in which V represents a hydrogen atom, an unsubstituted alkyl group having from 1 to 4 carbon atoms or a substituted alkyl group having at least one carboxy substituent;

U represents a methylene group;

$R^1$ represents a hydrogen atom or an alkyl group having from 1 to 4 carbon atoms;

$R^2$ and $R^4$ are the same or different and each represents a hydrogen atom or an alkyl group having from 1 to 3 carbon atoms;

$R^3$ represents a hydrogen atom or an alkyl group having from 1 to 4 carbon atoms;

$Y^1$ and $Y^2$ are the same or different and each represents a hydrogen atom, an aliphatic acyl group having from 2 to 4 carbon atoms, an unsubstituted aromatic acyl group or a sulfo group; and n is 1 or 2.

The most preferred compounds of the present invention are those compounds of formula (I) and salts thereof, in which:

A represents a group of formula (II) or (III), as defined above, particularly a group of formula (III);

W represents a methylene group or a group of formula $=C=N-OV$
  in which V represents a hydrogen atom, a carboxymethyl group or a 1-carboxy-1-methylethyl group, particularly a hydrogen atom, particularly we prefer that W should represent a methylene group;

U represents a methylene group;

$R^1$ represents a methyl group;

$R^2$ and $R^4$ are the same or different and each represents a hydrogen atom or a methyl group;

$R^3$ represents a methyl or t-butyl group, particularly a methyl group;

$Y^1$ and $Y^2$ are the same and each represents a hydrogen atom or an aliphatic acyl group having from 2 to 4 carbon atoms, particularly a hydrogen atom or an acetyl group; and n is 1.

Specific examples of the thiazolidine derivatives of the present invention are those compounds of formula (I-1) and (I-2), in which the substituents are as defined in the respective one of Tables 1 and 2, below, i.e. Table 1 relates to formula (I-1) and Table 2 relates to formula (I-2). In the Table, the following abbreviations are used:

| | |
|---|---|
| Ac | acetyl |
| Boz | benzoyl |
| iBu | isobutyl |
| tBu | t-butyl |
| Et | ethyl |
| Me | methyl |
| Oc | octyl |
| Ph | phenyl |
| Pn | pentyl |
| iPr | isopropyl |
| Sfo | sulfo |
| Tmb | 1,1,3,3-tetramethylbutyl |

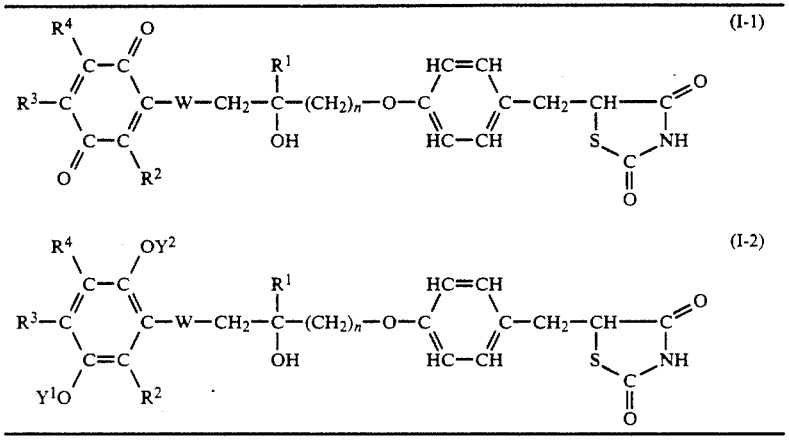

TABLE 1

| Cpd. No. | $R^1$ | $R^2$ | $R^3$ | $R^4$ | W | n |
|---|---|---|---|---|---|---|
| 1-1 | Me | Me | Me | Me | $CH_2$ | 1 |
| 1-2 | Me | Me | Me | Me | $CH_2$ | 2 |
| 1-3 | Me | Me | Me | Me | C=O | 1 |
| 1-4 | Me | Me | Me | Me | C=NOH | 1 |
| 1-5 | Me | Me | Me | Me | C=NOCOMe | 1 |
| 1-6 | Me | Me | Me | Me | C=NOCOPh | 1 |
| 1-7 | Me | Me | Me | Me | C=NOMe | 1 |
| 1-8 | Me | Me | Me | Me | C=NOCH$_2$Ph | 1 |
| 1-9 | Me | Me | Me | Me | C=NOCH$_2$(p-MePh) | 1 |
| 1-10 | Me | Me | Me | Me | C=NOCH$_2$COOH | 1 |
| 1-11 | Me | Me | Me | Me | C=NOCH$_2$COOEt | 1 |
| 1-12 | Me | Me | Me | Me | C=NOCMe$_2$COOH | 1 |
| 1-13 | Me | H | tBu | H | $CH_2$ | 1 |
| 1-14 | Me | H | tBu | H | $CH_2$ | 2 |
| 1-15 | Me | H | tBu | H | C=O | 1 |
| 1-16 | Me | H | tBu | H | C=NOH | 1 |
| 1-17 | Et | Me | Me | Me | $CH_2$ | 1 |
| 1-18 | iBu | Me | Me | Me | $CH_2$ | 1 |
| 1-19 | iBu | Me | Me | Me | C=O | 1 |
| 1-20 | Pn | Me | Me | Me | $CH_2$ | 1 |
| 1-21 | H | Me | Me | Me | $CH_2$ | 1 |
| 1-22 | Me | H | iPr | H | $CH_2$ | 1 |
| 1-23 | iBu | H | tBu | H | $CH_2$ | 1 |
| 1-24 | Oc | Me | Me | Me | $CH_2$ | 1 |
| 1-25 | Oc | Me | Me | Me | C=O | 1 |
| 1-26 | Me | H | Tmb | H | $CH_2$ | 1 |
| 1-27 | Me | H | Tmb | H | $CH_2$ | 2 |
| 1-28 | Me | H | Tmb | H | C=O | 1 |
| 1-29 | Me | H | Tmb | H | C=NOH | 1 |
| 1-30 | iBu | H | Tmb | H | C=NOCH$_2$COOH | 1 |
| 1-31 | Oc | H | Tmb | H | C=NOCH$_2$COOEt | 1 |

TABLE 2

| Cpd. No. | $Y^1$ | $Y^2$ | $R^1$ | $R^2$ | $R^3$ | $R^4$ | W | n |
|---|---|---|---|---|---|---|---|---|
| 2-1 | H | H | Me | Me | Me | Me | $CH_2$ | 1 |
| 2-2 | H | H | Me | Me | Me | Me | $CH_2$ | 2 |

TABLE 2-continued

| Cpd. No. | Y¹ | Y² | R¹ | R² | R³ | R⁴ | W | n |
|---|---|---|---|---|---|---|---|---|
| 2-3 | H | H | Me | Me | Me | Me | C=O | 1 |
| 2-4 | H | H | Me | Me | Me | Me | C=NOH | 1 |
| 2-5 | H | H | Me | Me | Me | Me | C=NOMe | 1 |
| 2-6 | H | H | Me | Me | Me | Me | C=NOCH₂COOH | 1 |
| 2-7 | H | H | Me | Me | Me | Me | C=NOC(Me)₂COOH | 1 |
| 2-8 | H | H | Et | Me | Me | Me | CH₂ | 1 |
| 2-9 | H | H | Me | H | tBu | H | CH₂ | 1 |
| 2-10 | H | H | H | H | H | H | CH₂ | 1 |
| 2-11 | H | H | iBu | H | H | H | C=O | 1 |
| 2-12 | Ac | Ac | Me | Me | Me | Me | CH₂ | 1 |
| 2-13 | Ac | Ac | Me | Me | Me | Me | CH₂ | 2 |
| 2-14 | Ac | Ac | Me | Me | Me | Me | C=O | 1 |
| 2-15 | Ac | Ac | Et | Me | Me | Me | C=NOH | 1 |
| 2-16 | Ac | H | Me | Me | Me | Me | CH₂ | 1 |
| 2-17 | Sfo | H | Me | Me | Me | Me | CH₂ | 1 |
| 2-18 | H | Ac | Me | Me | Me | Me | CH₂ | 1 |
| 2-19 | H | Sfo | Me | Me | Me | Me | CH₂ | 1 |
| 2-20 | Sfo | Sfo | Me | Me | Me | Me | CH₂ | 1 |
| 2-21 | Boz | Boz | Me | Me | Me | Me | CH₂ | 1 |

Of the compounds of the present invention, Compounds No. 1-1, 1-2, 1-4, 2-1, 2-4, 2-12, 2-13, 2-17 and 2-19 are preferred. The more preferred compounds are Compounds No.:

1-1. 5-{4-[2-hydroxy-2-methyl-4-(3,5,6-trimethyl-1,4-benzoquinon-2-yl)butoxy]benzyl}-2,4-dioxothiazolidine;

2-1. 5-{4-[4-(2,5-dihydroxy-3,4,6-trimethylphenyl)-2-hydroxy-2-methylbutoxy]benzyl}-2,4-dioxothiazolidine; and 2-12. 5-{4-[4-(2,5-diacetoxy-3,4,6-trimethylphenyl)-2-hydroxy-2-methylbutoxy]benzyl}-2,4-dioxothiazolidine.

Of these, the most preferred compound is Compound No. 1-1.

The compounds of the present invention may be prepared by a variety of methods well known for the preparation of compounds of this type. For example, in general terms, they may be prepared by the following steps:

(a) oxidizing a compound of formula (IV):

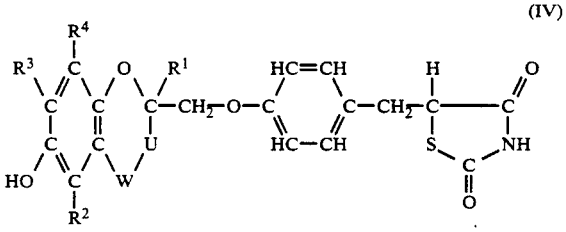

(in which R¹, R², R³, R⁴, U, W and n are as defined above), to give a compound of formula (V):

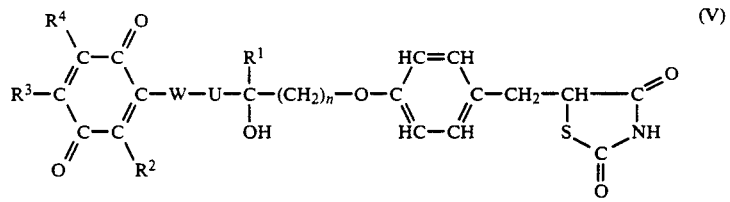

(in which R¹, R², R³, R⁴, U, W and n are as defined above);

(b) if required, reducing said compound of formula (V), to give a compound of formula (VI):

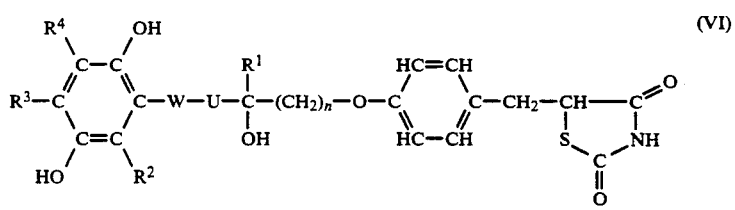

(in which R¹, R², R³, R⁴, U, W and n are as defined above);

(c) if required, protecting the hydroxy groups in the compound produced in any of steps (b), (d) or (e) to give a compound of formula (I) in which one or both of Y¹ and Y² represent hydroxy-protecting groups;

(d) if required, converting a group represented by W in the compound produced in any of steps (a), (b), (c) or (e) to any other group so represented; and (e) if required, salifying the compound produced in any of steps (a), (b), (c) and (d).

In step (a) of the above sequence, a compound of formula (V) is prepared by oxidizing a compound of formula (IV). The compound of formula (IV) is a known compound and is described, for example, in European Patent Publications No. 139 421 and 207 581, and in Japanese Patent Application Kokai No. Sho 61-36284, the disclosures of which are incorporated herein by reference.

The oxidation reaction may be carried out using any oxidizing agent known for the ring-opening oxidation of chromans and related compounds to benzoquinones, and examples of such oxidizing agents include: trivalent iron salts, such as ferric chloride, ferric bromide or ferric sulfate; divalent copper salts, such as cupric sulfate, cupric chloride or cupric acetate; and organic free radicals, such as compounds having an N-oxyl group, for example 2,2,6,6-tetramethylpiperidine-1-oxyl or 2,2,6,6-tetramethyl-4-oxopiperidine-1-oxyl. The reaction is normally and preferably carried out using from 0.5 to 15 moles, more preferably from 2 to 8 moles of the oxidizing agent per mole of the starting material of formula (IV). The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: ketones, such as acetone or methyl ethyl ketone; alcohols, such as methanol or ethanol; or a mixture of any one or more of these organic solvents with water. The reaction can take place over a wide range of temperatures, and the precise reaction temperature is not critical to the invention. In general, we find it convenient to carry out the reaction at a temperature of from 0° C. to 50° C., more preferably from 15° to 30° C. The time required for the reaction may also vary widely, depending on many factors, notably the reaction temperature and the nature of the reagents. However, provided that the reaction is effected under the preferred conditions outlined above, a period of from a few minutes to 30 hours, more preferably from 3 minutes to 20 hours, will usually suffice.

The resulting compound of formula (V) is a compound of the present invention and may be the desired final product. However, if it is desired to prepare a compound of formula (I) in which A represents a group of formula (II) and $Y^1$ and $Y^2$ both represent hydrogen atoms, i.e. a compound of formula (VI), this can be prepared by reduction of the compound of formula (V) in step (b).

The reduction reaction may be carried out by contacting the compound of formula (V) with a suitable reducing agent. There is no particular restriction on the nature of the reducing agent employed in this reaction, and any reducing agent capable of reducing a benzoquinone to a dihydroxybenzene compound may equally be employed here. Examples of especially suitable reducing agents include the metal borohydrides, especially alkali metal borohydrides, such as sodium borohydride or potassium borohydride. The amount of reducing agent is not critical to the reaction, although, for economy, it is preferred that the amount should be at least equimolar with respect to the compound of formula (V). In general, the reaction is normally carried out using from 1 to 20 moles, and preferably a large excess of the reducing agent, per mole of the compound of formula (V). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, propanol, butanol or ethylene glycol monomethyl ether; and ethers, such as tetrahydrofuran or dioxan. The reaction can take place over a wide range of temperatures, and the precise reaction temperature is not critical to the invention. In general, we find it convenient to carry out the reaction at a temperature of from 0° C. to 100° C. The time required for the reaction may also vary widely, depending on many factors, notably the reaction temperature and the nature of the reagents and of the solvent. However, provided that the reaction is effected under the preferred conditions outlined above, a period of from a few minutes to 30 hours will usually suffice.

In step (b), where W represents a carbonyl group, the reduction may be carried out without protecting the carbonyl group, but we prefer that the carbonyl group should be protected prior to this reaction. There is no particular restriction on the nature of the carbonyl-protecting group, provided that it has no adverse effect on the reduction reaction. Examples of suitable carbonyl-protecting groups include those groups of formula —X—$(CH_2)_p$—X— (in which X represents an oxygen or sulfur atom and p is 2 or 3), for example the ethylenedioxy, trimethylenedioxy, ethylenedithio and trimethylenedithio groups. Such protecting groups can be derived from the corresponding glycols of formula H—X—$(CH_2)_p$—X—H, for example ethylene glycol, trimethylene glycol, ethylene dithioglycol or trimethylene dithioglycol, in the presence of an acid catalyst, such as hydrogen chloride or sulfuric acid. The compounds having a protected carbonyl group may then be subjected to reduction, as described above, after which the protecting group may be removed according to conventional means to afford the desired compound of formula (VI).

Where W represents a group of formula =C=N—OV (in which V is as defined above), the desired compound of formula (VI) can be prepared by reduction as described above in step (b), keeping the group of formula =C=N—OV intact. However, we prefer instead to prepare the corresponding compound of formula (VI) in which W represents a carbonyl group, and then to convert that carbonyl group to the group of formula =C=N—OV. This may be achieved by reacting the compound of formula (VI) in which W represents a carbonyl group with an oximating agent, for example a hydroxylamine of formula $H_2N$—OV (in which V is as defined above) or with a salt thereof, which may be a salt with an inorganic or organic acid. The reaction may be carried out according to the procedure described in European Patent Publication No. 207 581. In the reaction of the compound of formula (VI) in which W represents a carbonyl group with a hydroxylamine of formula $H_2N$—OV (in which V is as defined above), there is no particular limitation on the molar ratio of the reagents to each other. However, we prefer that the reaction should be carried out using an equimolar amount or an excess, preferably a large excess of the oximating agent, e.g. from 1 to 50 moles of hydroxylamine per mole of the compound of formula (VI). Where the hydroxylamine of formula $H_2N$—OV is employed in the form of a salt of an inorganic acid, the reaction is preferably carried out in the presence of an acid-binding agent. Examples of suitable acid-binding agents include: alkali metal hydroxides, such as sodium hydroxide or potassium hydroxide; and alkali metal carbonates, such as sodium carbonate or potassium carbonate. The amount of the acid-binding agent employed is preferably not more than one mole equivalent per mole of the inorganic acid salt. The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, propanol, butanol or ethylene glycol monomethyl ether; ethers, such as tetrahydrofuran or dioxan; amides, especially dialkylformamides, such as dimethylformamide or dimethylacetamide; sulfoxides, such as dimethyl sulfoxide; sulfones, such as sulfolane; organic bases, such as triethylamine or pyridine; water; or a mixture of any two or more of these solvents. The reaction can take place over a wide range of temperatures, and the precise reaction temperature employed is not critical to the invention. In general, we find it convenient to carry out the reaction at a temperature of from 0° to 100° C. The time required for the reaction may also vary widely, depending on many factors, notably the reaction temperature and the nature of the reagents and of the solvent. However, provided that the reaction is effected under the preferred conditions outlined above, a period of from a few minutes to about 10 days will usually suffice.

The compound of formula (VI) in which W represents a carbonyl group can, if desired, be prepared by treating the corresponding compound of formula (VI) in which W represents a group of formula =C=N—OV (in which V is as defined above) with an acid. Suitable acids include inorganic acids, such as hydrochloric acid, hydrobromic acid or sulfuric acid. The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, propanol, butanol or ethylene glycol monomethyl ether; ethers, such as tetrahydrofuran or dioxan; amides, especially dialkylformamides, such as dimethylformamide or dimethylacetamide; sulfoxides, such as dimethyl sulfoxide; sulfones, such as sulfolane; organic bases, such as triethylamine or pyridine; water; or a mixture of any two or more of these solvents. The reaction can take place over a wide range of temperatures, and the precise reaction temperature is not critical to the invention. In general, we find it convenient to carry out the reaction at a temperature of from 20° to 100° C. The time required for the reaction may also vary widely, depending on many factors, notably the reaction temperature and the nature of the reagents. However, provided that the reaction is effected under the preferred conditions outlined above, a period of from a few minutes to a few days will usually suffice.

In step (c), one or both of the hydroxy groups of the compounds [formula (I) in which $Y^1$ and $Y^2$ both represent hydrogen atoms] can be protected by conventional means. As is well known in the art, the nature of the reaction employed to protect these groups will depend on the nature of the protecting group to be introduced.

For example, where the hydroxy-protecting group is an aliphatic or aromatic acyl group, the reaction can be carried out by using an acylating agent, e.g. as described in European Patent Publication No. 207 581. That is to say, acylation can be carried out using a reactive derivative of the organic acid corresponding to the acyl group which it is desired to introduce, for example an acid anhydride or acid halide thereof. There is no particular limitation on the molar ratio of the acylating agent to the starting material, but the reaction is preferably carried out using a molar excess of the acylating agent, preferably from 1 to 10 moles of the acylating agent per mole of the starting material. The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxan; aromatic hydrocarbons, such as benzene, toluene or xylene; aliphatic and cycloaliphatic hydrocarbons, such as hexane, cyclohexane or heptane; halogenated hydrocarbons, especially halogenated aliphatic hydrocarbons, such as methylene chloride or chloroform; organic bases, such as pyridine or triethylamine; amides, especially dialkylformamides, such as dimethylformamide or dimethylacetamide; sulfoxides, such as dimethyl sulfoxide; sulfones, such as sulfolane; water; or a mixture of any two or more of these solvents. The reaction can take place over a wide range of temperatures, and the precise reaction temperature is not critical to the invention. In general, we find it convenient to carry out the reaction at a temperature of from 0° to 100° C. The time required for the reaction may also vary widely, depending on many factors, notably the reaction temperature and the nature of the reagents and of the solvents. However, provided that the reaction is effected under the preferred conditions outlined above, a period of from a few minutes to about 20 hours will usually suffice.

Where the hydroxy-protecting group is a heterocyclic group such as a tetrahydropyranyl, tetrahydrothiopyranyl, tetrahydrofuranyl or tetrahydrothienyl group, the protection reaction may be effected by reacting the starting material with a corresponding heterocyclic compound, such as dihydropyran, dihydrothiopyran, dihydrothiophene or 4-methoxy-5,6-dihydro(2H)-pyran. The reaction is normally and preferably carried out in the presence of a small amount of an inorganic acid, such as hydrochloric acid, sulfuric acid, phosphoric acid or phosphorous oxychloride, or of an organic acid, such as p-toluenesulfonic acid, trifluoroacetic acid, picric acid or benzenesulfonic acid. The reaction is also normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran; nitriles, such as acetonitrile; halogenated hydrocarbons, especially halogenated aliphatic hydrocarbons, such as chloroform or methylene chloride; and amides, especially dialkylformamides, such as dimethylformamide. The reaction can take place over a wide range of temperatures, and the precise reaction temperature is not critical to the invention. In general, we find it convenient to carry out the reaction at a temperature of from 0° C. to about room temperature. The time required for the reaction may also vary widely, depending on many factors, notably the reaction temperature and the nature of the reagents and of the solvents to be employed. However, provided that the reaction is effected under the preferred conditions outlined above, a period of from 30 minutes to about 8 hours will usually suffice.

Where the hydroxy-protecting group is a silyl group, the protection reaction can be effected by reacting the starting material with a silyl compound, whose nature depends on the nature of the protecting group to be introduced, preferably a silyl halide, more preferably chloride, such as trimethylsilyl chloride, dimethyl-t-butylsilyl chloride or diphenyl-t-butylsilyl chloride. The reaction is preferably carried out in the presence of an organic base, such as triethylamine, dimethylaminopyridine, imidazole or pyridine, or of a sulfide, such as lithium sulfide. The reaction is also normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran; nitriles, such as acetonitrile; halogenated hydrocarbons, especially halogenated aliphatic hydrocarbons, such as chloroform or methylene chloride; amides, especially dialkylformamides, such as dimethylformamide; and organic bases, such as triethylamine or pyridine. The reaction can take place over a wide range of temperatures, and the precise reaction temperature is not critical to the invention. In general, we find it convenient to carry out the reaction at a temperature of from 0° C. to about room temperature. The time required for the reaction may also vary widely, depending on many factors, notably the reaction temperature and the nature of the reagents and of the solvents to be employed. However, provided that the reaction is effected under the preferred conditions outlined above, a period of from 30 minutes to about 8 hours will usually suffice.

Where the hydroxy-protecting group is an alkoxyalkyl or aralkyl group, the protection reaction can be effected by reacting the starting material with an alkoxyalkylating or aralkylating agent. The reaction may be carried out according to the procedure described in European Patent Publication No. 207 581. That is, the reaction is carried out using an alkoxyalkyl halide (preferably the bromide), such as chloromethyl methyl ether, as the alkoxyalkylating agent or using an aralkyl halide (preferably the bromide), such as benzyl chloride or benzyl bromide, as the aralkylating agent. There is no particular limitation on the molar ratio of the alkoxyalkylating or aralkylating agent to the starting material, but the reaction is preferably effected using a molar excess of the alkoxyalkylating or aralkylating agent, preferably from 1 to 10 moles of the alkoxy-alkylating or aralkylating agent per mole of the starting material. The reaction is preferably carried out in the presence of a base, the nature of which is not critical, provided that it does not adversely affect other parts of the molecule. Examples of suitable bases include: alkali metal carbonates or bicarbonates, such as sodium carbonate, potassium carbonate, sodium bicarbonate or potassium bicarbonate; alkali metal hydroxides or alkaline earth metal hydroxides, such as sodium hydroxide, potassium hydroxide or calcium hydroxide; alkali metal hydrides, such as sodium hydride or potassium hydride; alkali metal alkoxides, such as sodium methoxide, sodium ethoxide or potassium t-butoxide; organic lithium compounds, such as butyl lithium or t-butyl lithium; lithium dialkylamides, such as lithium diisopropylamide or lithium dicyclohexylamide; and organic bases, such as pyridine or triethylamine. Of these, the alkali metal carbonates, such as potassium carbonate, are preferred. The reaction is preferably carried out using from 1 to 10 moles of the base per mole of the starting material, and the reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxan; aliphatic hydrocarbons, such as hexane, heptane or cyclohexane; aromatic hydrocarbons, such as benzene, toluene or xylene; halogenated hydrocarbons, especially halogenated aliphatic hydrocarbons, such as methylene chloride or chloroform; alcohols, such as methanol, ethanol or t-butanol; ketones, such as acetone or methyl ethyl ketone; organic bases, such as pyridine or triethylamine; amides, such as dimethylformamide or dimethylacetamide; sulfoxides, such as dimethyl sulfoxide; sulfones, such as sulfolane; water; or a mixture of any two or more of these solvents. The reaction can take place over a wide range of temperatures, and the precise reaction temperature is not critical to the invention. In general, we find it convenient to carry out the reaction at a temperature of from −10° C. to 100° C. The time required for the reaction may also vary widely, depending on many factors, notably the reaction temperature and the nature of the reagents and of the solvents to be employed. However, provided that the reaction is effected under the preferred conditions outlined above, a period of from a few minutes to a few days will usually suffice.

Where the hydroxy-protecting group is an alkoxycarbonyl group, the protection reaction may be carried out by reacting the starting material with an alkoxycarbonyl halide, such as an alkoxycarbonyl chloride. The reaction is normally and preferably carried out in the presence of an organic base, especially a tertiary amine base, such as trimethylamine, triethylamine or pyridine. The reaction is also normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxan; aromatic hydrocarbons, such as benzene, toluene or xylene; aliphatic hydrocarbons, such as hexane, heptane or cyclohexane; organic bases, such as pyridine or triethylamine; amides, such as dimethylformamide or dimethylacetamide; sulfoxides, such as dimethyl sulfoxide; and sulfones, such as sulfolane. The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents and of the solvents to be employed. However, provided that the reaction is effected under the preferred conditions outlined above, a period of from a few minutes to a few days will usually suffice.

Where the hydroxy-protecting group is a sulfo group, the protection reaction can be carried out by reacting the starting material with a sulfonating agent. This reaction may be carried out according to the procedure described in Japanese Patent Application Kokai No. Sho 62-123186, the disclosure of which is incorporated herein by reference. That is, the starting material is contacted with chlorosulfonic acid in the presence of an organic base, such as pyridine, picoline, lutidine or triethylamine. There is no particular limitation on the molar ratio of the chlorosulfonic acid to the starting material, but the reaction is preferably carried out using from 0.5 to 10 moles of chlorosulfonic acid per mole of the starting material. The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; esters, such as ethyl acetate; nitriles, such as acetonitrile; and mixtures of any two or more of these solvents. The reaction can take place over a wide range of temperatures, and the precise reaction temperature is not critical to the invention. In general, we find it convenient to carry out the reaction at a temperature of from 50° C. to 100° C. The time required for the reaction may also vary widely, depending on many factors, notably the reaction temperature and the nature of the reagents and of the solvent to be employed. However, provided that the reaction is effected under the preferred conditions outlined above, a period of from 10 minutes to 2 hours will usually suffice.

Alternatively the sulfo protecting group may be introduced by esterification of the starting material using sulfuric acid in the presence of a dehydrating agent. Examples of dehydrating agents include: carbodiimides, such as N,N-dicyclohexylcarbodiimide (DCC), 1-(3-dimethylaminopropyl)-3-ethylcarbodiimide or a mineral acid salt thereof, such as the hydrochloride; of these, 1-(3-dimethylaminopropyl)-3-ethylcarbodiimide is preferred. In the esterification, the reaction is preferably carried out using from 1 to 5 moles, more preferably from 1 to 2 moles, of sulfuric acid per mole of the starting material, and from 1 to 10 moles, more preferably from 3 to 6 moles, of the dehydrating agent per mole of the starting material. The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; ethers, such as tetrahydrofuran or dioxan; halogenated hydrocarbons, especially halogenated aliphatic hydrocarbons, such as methylene chloride or chloroform; nitriles, such as acetonitrile; amides, especially dialkylformamides, such as dimethylformamide or dimethylacetamide; sulfoxides, such as dimethyl sulfoxide; sulfones, such as sulfolane; water; and mixtures of any two or more of these solvents; the amides are preferred. The reaction can take place over a wide range of temperatures, and the precise reaction temperature is not critical to the invention. In general, we find it convenient to carry out the reaction at a temperature of from 0° C. to 50° C., more preferably at about room temperature. The time required for the reaction may also vary widely, depending on many factors, notably the reaction temperature and the nature of the reagents and of the solvent to be employed. However, provided that the reaction is effected under the preferred conditions outlined above, a period of from 10 minutes to 2 days, more preferably from 1 to 3 hours will usually suffice.

After completion of the reaction, the desired compounds can be recovered from the reaction mixture by conventional means. For example, one suitable recovery procedure comprises: extracting the compound from the reaction mixture by adding a suitable solvent; and freeing the extracts from the solvents by distillation. The resulting product can then, if desired, be further purified by conventional means, for example recrystallization, reprecipitation or the various chromatography techniques, notably column chromatography, preferably through silica gel.

Also, if desired, resolution of the individual isomers can be carried out by conventional means at any appropriate time.

The thiazolidine compounds of the present invention exhibited the ability to lower blood-sugar levels in a test system using genetically hyperglycemic animals and exhibited inhibitory activities against aldose reductase in the test system prescribed by Varma et al. [S. D. Varma and H. Kinoshita, Biochem. Pharmac., 25, 2505 (1976)]. The compounds also demonstrated a low toxicity. Accordingly, the compounds of the invention may be used for the treatment and prophylaxis of various diseases and disorders arising from imbalances in the blood sugar level in mammals, especially human beings, for example human hyperlipemia, diabetes and their complications, for example diabetic cataracts, diabetic neurosis and the like.

The compounds of the present invention can be administered in various forms, depending on the disorder to be treated and the condition of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as a vehicle, a binder, a disintegrator, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, for the treatment of hyperlipemia and/or diabetes or complications thereof, a daily dosage of from 5 to 5000 mg of the compound is recommended for an adult human patient, and this may be administered in a single dose or in divided doses.

The preparation of the compounds of the present invention is further illustrated by the following non-limiting Examples. The subsequent Experiment illustrates the biological activity of the compounds of the invention.

EXAMPLE 1

5-{4-[2-Hydroxy-2-methyl-4-(3,5,6-trimethyl-1,4-benzoquinon-2-yl)butoxy]benzyl}-2,4-dioxothiazolidine 15 ml of an aqueous solution of ferric chloride acidified with hydrochloric acid [a mixture of about 65% by weight of ferric chloride ($FeCl_3.6H_2O$) and about 35% by weight of concentrated hydrochloric acid] were added dropwise, whilst ice-cooling and stirring, to a solution of 6.3 g of 5-[4-(6-hydroxy-2,5,7,8-tetramethylchroman-2-ylmethoxy)benzyl]-2,4-dioxothiazolidine dissolved in 50 ml of acetone, and the resulting mixture was allowed to stand overnight at room temperature. At the end of this time, the reaction mixture was diluted with 500 ml of water and then extracted with ethyl acetate. The extracts were combined, washed with a saturated aqueous solution of sodium chloride and dried over anhydrous sodium sulfate, and the solvent was then removed by distillation under reduced pressure. The resulting residue was then purified by column chromatography through silica gel, using a 5:1 by volume mixture of benzene and ethyl acetate as the eluent, to afford 4.2 g of the title compound as a yellow powder softening at 55°–65° C.

Nuclear Magnetic Resonance Spectrum (hexadeuterated acetone) δ ppm:
1.35 (3H, singlet);
1.5–1.85 (2H, multiplet);
1.97 (6H, singlet);
2.05 (3H, singlet);
2.4–2.9 (2H, not determined);
3.11 (1H, doublet of doublets, J=9 & 15 Hz);
3.45 (1H, doublet of doublets, J=3 & 15 Hz);
3.85 (2H, broad);
4.80 (1H, doublet of doublets, J=3 & 9 Hz);
6.90 (2H, doublet, J=9 Hz);
7.25 (2H, doublet, J=9 Hz).

EXAMPLE 2

5-{4-[2-Hydroxy-4-hydroxyimino-2-methyl-4-(3,5,6-trimethyl-1,4-benzoquinon-2-yl)butoxy]benzyl}-2,4-dioxothiazolidine The procedure of Example 1 was repeated, but using 2 g of 5-[4-(6-hydroxy-4-hydroxyimino-2,5,7,8-tetramethylchroman-2-ylmethoxy)benzyl]-2,4-dioxothiazolidine, 15 ml of acetone and 5 ml of an aqueous solution of ferric chloride acidified with hydrochloric acid (a mixture of about 65% by weight of $FeCl_3.6H_2O$ and about 35% by weight of concentrated hydrochloric acid), to afford 0.74 g of the title compound as a yellow powder softening at 80°–85° C.

Nuclear Magnetic Resonance Spectrum (hexadeuterated dimethyl sulfoxide) δ ppm:
1.19 (3H, singlet);
1.79 (3H, broad singlet);
1.84 (3H, broad singlet);
1.97 (3H, singlet);
2.8–3.0 (2H, multiplet);
3.03 (1H, doublet of doublets, J=9 & 14 Hz);
3.25–3.4 (1H, not determined);
3.53 (1H, doublet, J=9 Hz);
3.62 (1H, doublet, J=9 Hz);
4.7–4.85 (1H, broad, disappeared on adding deuterium oxide);
4.85 (1H, doublet of doublets, J=4 & 9 Hz);
6.71 (2H, doublet, J=8.5 Hz);
7.09 (2H, doublet, J=8.5 Hz);
11.41 (1H, singlet, disappeared on adding deuterium oxide);
11.99 (1H, singlet, disappeared on adding deuterium oxide).

EXAMPLE 3

5{4-[4-(2,5-Dihydroxy-3,4,6-trimethylphenyl)-2-hydroxy-2-methylbutoxy]benzyl}-2,4-dioxothiazolidine 165 mg of sodium borohydride were added, whilst ice-cooling and stirring, to a solution of 1 g of 5-{4-[2-hydroxy-2-methyl-4-(3,5,6-trimethyl-1,4-benzoquinon-2-yl)butoxy]benzyl}-2,4-dioxothiazolidine (prepared as described in Example 1) dissolved in 10 ml of ethanol, and the resulting mixture was stirred at room temperature for 30 minutes. At the end of this time, the reaction mixture was poured into a mixture of 100 ml of ice-water and 0.6 ml of 35% v/v aqueous hydrochloric acid to precipitate white crystals. The crystals were collected by filtration and dried in vacuo over phosphorous pentoxide to afford 0.9 g of the title compound as a yellow powder melting at 84°–88° C.

Nuclear Magnetic Resonance Spectrum (hexadeuterated dimethyl sulfoxide) δ ppm:
1.24 (3H, singlet);
1.5–1.65 (2H, multiplet);
2.03 (6H, singlet);
2.05 (3H, singlet);
2.58–2.65 (2H, multiplet);
3.05 (1H, doublet of doublets, J=9 & 14 Hz);
3.25–3.35 (1H, not determined);
3.74 & 3.78 (2H, AB type, J=9 Hz);
4.66 (1H, singlet, disappeared on adding deuterium oxide);
4.86 (1H, doublet of doublets, J=4 & 9 Hz);
6.88 (2H, doublet, J=9 Hz);
7.15 (2H, doublet, J=9 Hz);
7.24 (1H, singlet, disappeared on adding deuterium oxide);
7.26 (1H, singlet, disappeared on adding deuterium oxide);
11.98 (1H, broad singlet, disappeared on adding deuterium oxide).

EXAMPLE 4

5-{4-[4-(2,5-Diacetoxy-3,4,6-trimethylphenyl)-2-hydroxy-2-methylbutoxy]benzyl}-2,4-dioxothiazolidine 0.8 g of acetic anhydride was added to a mixture of 0.9 g of 5-{4-[4-(2,5-dihydroxy-3,4,6-trimethylphenyl)-2-hydroxy-2-methylbutoxy]benzyl}-2,4-dioxothiazolidine (prepared as described in Example 3) and 7 ml of pyridine, and the resulting mixture was allowed to stand at room temperature for 3 days. At the end of this time, the reaction mixture was poured into 50 ml of water and then extracted with ethyl acetate. The extracts were washed, in turn, with 0.1N aqueous hydrochloric acid and with a saturated aqueous solution of sodium chloride, and dried over anhydrous sodium sulfate. The solvent was then removed by distillation under reduced pressure. The resulting residue was then subjected to column chromatography through silica gel, using a 7:3 by volume mixture of benzene and ethyl acetate as the eluent, to afford 0.3 g of the title compound as a white powder softening at 94°–97° C.

Nuclear Magnetic Resonance Spectrum (hexadeuterated dimethyl sulfoxide) δ ppm:
1.23 (3H, singlet);
1.4–1.7 (2H, broad);

1.95 (3H, singlet);
1.98 (3H, singlet);
1.99 (3H, singlet);
2.22 (3H, singlet);
2.3–2.7 (2H, not determined);
2.34 (3H, singlet);
3.05 (1H, doublet of doublets, J=9 & 14 Hz);
3.2–3.4 (1H, not determined);
3.72 (1H, doublet, J=9 Hz);
3.79 (1H, doublet, J=9 Hz);
4.72 (1H, singlet);
4.86 (1H, doublet of doublets, J=4 & 9 Hz);
6.91 (2H, doublet, J=9 Hz);
7.15 (2H, doublet, J=9 Hz);
11.98 (1H, broad singlet).

EXAMPLE 5

(A) Mono-potassium salt of 5-{4-[4-(2-hydroxy-5-sulfoxy-3,4,6-trimethylphenyl)-2-hydroxy-2-methylbutoxy[benzyl]}-2,4-dioxothiazolidine and (B) mono-potassium salt of 5-{4-[4-(5-hydroxy-2-sulfoxy-3,4,6-trimethylphenyl)-2-hydroxy-2-methylbutoxy}benzyl]-2,4-dioxothiazolidine 0.26 g of chlorosulfonic acid were added to a mixture of 1.0 g of 5-{4-[4-(2,5-dihydroxy-3,4,6-trimethylphenyl)-2-hydroxy-2-methylbutoxy]benzyl}-2,4-dioxothiazolidine (prepared as described in Example 3), 0.35 g of pyridine and 10 ml of acetonitrile, and the resulting mixture was heated at 80° C. for 3 hours. At the end of this time, the reaction mixture was cooled and the supernatant was removed by decantation. The residual oily material was washed with 10 ml of ethyl acetate. The oil thus obtained was mixed with 5 ml of water and its pH was adjusted to a value of about 6.5 by the addition of an approximately 2N aqueous solution of potassium hydroxide, after which ethyl acetate was added. The ethyl acetate-soluble material was removed, and then the aqueous layer was lyophilized to afford a crude product as a white powder. The crude product was purified by ion-exchange chromatography through Diaion HP-20 (trade mark for a product of Mitsubishi Chemical Industries, Co.) using a 85:15 by volume mixture of water and acetonitrile as the eluent to afford the title compound as a white powder.

Mass spectrum (m/e, negative fast atom bombardment method using m-nitrobenzyl alcohol as a matrix; M denotes the molecular weight): $(M-H)^- = 576$, $(M-K)^- = 538$.

The nuclear magnetic resonance spectrum ($\delta$ ppm, in hexadeuterated dimethyl sulfoxide) shows that the product thus obtained is an approximately 1:1 mixture of the isomers (A) and (B), based upon the specific signals: 4.80 (1H, quartet), 4.67 (0.5H, singlet) and 4.45 (0.5H, singlet).

EXPERIMENT

Inhibition of Activity of Aldose Reductase

The inhibition of the activity of aldose reductase is well recognised as a test to indicate the ability of a compound to reduce diabetic complications.

Aldose reductase was separated and partially purified from rat lenses by the method of Hyman and Kinoshita [J. Biol. Chem., 240, 877 (1965)]. Enzyme activities were photometrically determined by the method of Varma et al. [Biochem. Pharmac., 25, 2505 (1976)]. The inhibition of aldose reductase activity was determined by employing each test compound in various concentrations. The compound of Example 1 herein showed an $IC_{50}$ of 0.82, whilst the known compound, 5-[4-(6-hydroxy-2,5,7,8-tetramethylchroman-2-ylmethoxy)benzyl]-thiazolidine-2,4-dione (which is disclosed in Example 2 of European Patent Publication No. 139 421, and is amongst the closest of the prior art compounds) showed an $IC_{50}$ of 2.07, indicating substantially lower activity.

We claim:
1. A compound of formula (I):

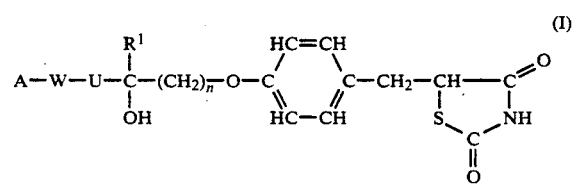

in which:

A represents a group of formula (II) or (III):

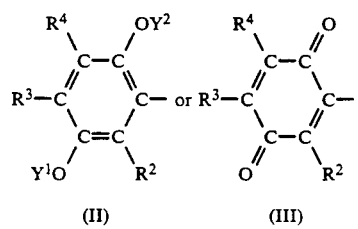

W represents a methylene group (>CH₂), a carbonyl group (>C=O) or a group of formula >C=N—OV
   in which V represents a hydrogen atom, a sulfo group, an acyl group as defined below or an alkyl group which has from 1 to 8 carbon atoms and which is unsubstituted or has at least one substituent selected from the group consisting of substituents (a), defined below;

U represents a methylene group; or W is absent and U represents a carbon-carbon double bond between the group represented by A and the group —CR¹(OH)—;

R¹ represents a hydrogen atom or an alkyl group having from 1 to 8 carbon atoms;

R² and R⁴ are independently selected from the group consisting of hydrogen atoms and alkyl groups having from 1 to 8 carbon atoms;

R³ represents a hydrogen atom or an alkyl group having from 1 to 10 carbon atoms;

Y¹ and Y² are independently selected from the group consisting of hydrogen atoms and hydroxy-protecting groups, said hydroxy-protecting groups being: aliphatic acyl groups having from 1 to 25 carbon atoms; halogenated alkanoyl groups having from 2 to 6 carbon atoms; alkoxyalkanoyl groups in which the alkoxy part has from 1 to 5 carbon atoms and the alkanoyl part has from 2 to 6 carbon atoms; alkenoyl or alkynoyl groups having from 3 to 6 carbon atoms; aromatic acyl groups in which the aryl part has from 6 to 14 ring carbon atoms and is a carbocyclic group, which is unsubstituted or has from 1 to 5 substituents selected from the group consisting of substituents (c), defined below; heterocyclic groups having 5 or 6 ring atoms, of which 1 or 2 are hetero-atoms selected from the group consisting of oxygen, sulfur and nitrogen atoms, which groups may be unsubstituted or may have at least one substituent selected from the group consisting of substituents (c), defined below, and oxygen atoms; tri-substituted silyl groups, in which all three or two or one of the substituents are alkyl groups having from 1 to 5 carbon atoms, and none, one or two of the substituents are aryl groups, as defined above; alkoxyalkyl groups, in which the alkoxy and alkyl parts each have from 1 to 5 carbon atoms; alkoxy-substituted alkoxymethyl groups in which each alkoxy part has from 1 to 5 carbon atoms; halogenated alkoxymethyl groups in which the alkoxy part has from 1 to 5 carbon atoms; halogenated ethyl groups; arylselenyl-substituted ethyl groups, in which the aryl part is as defined above; aralkyl groups in which the alkyl part has from 1 to 5 carbon atoms and the aryl part is a carbocyclic aryl group which has from 6 to 14 ring carbon atoms and which may be unsubstituted or substituted on the aryl part with an alkyl group, an alkoxy group, a nitro group, a halogen atom, a cyano group, or an alkylenedioxy group having from 1 to 3 carbon atoms; alkoxycarbonyl groups having from 2 to 7 carbon atoms and which are unsubstituted or substituted with a halogen atom or a tri-substituted silyl group, as defined above; alkenyloxycarbonyl groups in which the alkenyl part has from 2 to 6 carbon atoms; sulfo groups; and aralkyloxycarbonyl groups, in which the aralkyl part is as defined above;

n is 1, 2 or 3;

said acyl group included in the definition of V is: an unsubstituted aliphatic acyl group which contains from 1 to 6 carbon atoms; a substituted aliphatic acyl group which contains from 2 to 6 carbon atoms and which is substituted with at least one substituent selected from the group consisting of substituents (b), defined below; an aromatic acyl group in which the aryl part is a carbocyclic aromatic ring which has from 6 to 14 ring carbon atoms and which is unsubstituted or has at least one substituent selected from the group consisting of substituents (c), defined below; or a heterocyclic acyl group having a heterocyclic ring containing 5 or 6 ring atoms, of which 1, 2 or 3 are hetero-atoms selected from the group consisting of nitrogen, oxygen and sulfur atoms, the heterocyclic ring being unsubstituted or having at least one substituent selected from the group consisting of substituents (c), defined below, and oxygen atoms;

said substituents (a) are selected from the group consisting of alkoxycarbonyl groups having from 2 to 6 atoms, carboxy groups and carbocyclic aryl groups which have from 6 to 10 ring carbon atoms and which are unsubstituted or have at least one substituent selected from the group consisting of substituents (c), defined below;

said substituents (b) are selected from the group consisting of halogen atoms and alkoxy groups having from 1 to 5 carbon atoms;

said substituents (c) are selected from the group consisting of alkyl groups having from 1 to 5 carbon atoms, alkoxy groups having from 1 to 5 carbon atoms, halogen atoms, halogenated alkyl groups having from 1 to 3 carbon atoms, nitro groups, hydroxy groups, alkoxycarbonyl groups having from 2 to 6 carbon atoms and aryl groups which have from 6 to 10 ring carbon atoms and which are unsubstituted or have at least one substituent selected from the group consisting of substituents (d), defined below; and said substituents (d) are selected from the group consisting of alkyl groups having from 1 to 5 carbon atoms, alkoxy groups having from 1 to 5 carbon atoms, halogen atoms, halogenated alkyl groups having from 1 to 3 carbon atoms, nitro groups and hydroxy groups;

and salts thereof.

2. The compound of claim 1, wherein W represents a methylene group, a carbonyl group or a group of formula $=C=N-OV$ in which V represents: a hydrogen atom; a sulfo group; an unsubstituted alkyl group having from 1 to 4 carbon atoms; a substituted alkyl group having from 1 to 4 carbon atoms in which the substituents are selected from the group consisting of aryl groups which have from 6 to 10 ring carbon atoms and which are unsubstituted or are substituted by at least one alkyl substituent having from 1 to 5 carbon atoms, carboxy groups and alkoxycarbonyl groups having from 2 to 6 carbon atoms; an aliphatic carboxylic acyl group having from 1 to 6 carbon atoms; or a carbocyclic aromatic carboxylic acyl group in which the aryl part has 6 or 10 ring carbon atoms, said group being unsubstituted or having at least one substituent selected from the group consisting of substituents (c), defined in claim 1.

3. The compound of claim 2, wherein V represents a hydrogen atom, an aliphatic acyl group having from 1 to 6 carbon atoms, an aromatic acyl group or the sulfo group.

4. The compound of claim 3, wherein V represents a hydrogen atom, an aliphatic acyl group having from 2 to 4 carbon atoms, an unsubstituted aromatic acyl group or the sulfo group.

5. The compound of claim 4, wherein V represents a hydrogen atom or an aliphatic acyl group having from 2 to 4 carbon atoms.

6. The compound of claim 5, wherein V represents a hydrogen atom or the acetyl group.

7. The compound of claim 1, wherein $R^1$ represents a hydrogen atom or an alkyl group having from 1 to 4 carbon atoms.

8. The compound of claim 1, wherein $R^2$ and $R^4$ are the same or different and each represents a hydrogen atom or an alkyl group having from 1 to 3 carbon atoms.

9. The compound of claim 1, wherein $R^3$ represents a hydrogen atom or an alkyl group having from 1 to 4 carbon atoms.

10. The compound of claim 1, wherein $Y^1$ and $Y^2$ are the same or different and each represents a hydrogen atom, an aliphatic acyl group having from 1 to 6 carbon atoms, an aromatic acyl group, as defined in claim 1, or a sulfo group.

11. The compound of claim 1 wherein:

A represents a group of formula (II) or (III), as defined in claim 1;

W represents a methylene group, a carbonyl group or a group of formula $=C=N-OV$ in which V represents a hydrogen atom, an unsubstituted alkyl group having from 1 to 4 carbon atoms or a substituted alkyl group having from 1 to 4 carbon atoms in which the substituents are selected from the group consisting of aryl groups which have from 6 to 10 ring carbon atoms and which are unsubstituted or are substituted by at least one alkyl substituent having from 1 to 5 carbon atoms, carboxy groups and alkoxycarbonyl groups having from 2 to 6 carbon atoms;

U represents a methylene group;

$R^1$ represents a hydrogen atom or an alkyl group having from 1 to 4 carbon atoms;

$R^2$ and $R^4$ are the same or different and each represents a hydrogen atom or an alkyl group having from 1 to 3 carbon atoms;

$R^3$ represents a hydrogen atom or an alkyl group having from 1 to 4 carbon atoms;

$Y^1$ and $Y^2$ are the same or different and each represents a hydrogen atom, an aliphatic acyl group having from 1 to 6 carbon atoms, an aromatic acyl group, as defined in claim 1, or a sulfo group; and n is 1 or 2.

12. The compound of claim 1, wherein:

A represents a group of formula (II) or (III), as defined in claim 1;

W represents a methylene group or a group of formula $=C=N-OV$ in which V represents a hydrogen atom, an unsubstituted alkyl group having from 1 to 4 carbon atoms or a substituted alkyl group having at least one carboxy substituent;

U represents a methylene group;

$R^1$ represents a hydrogen atom or an alkyl group having from 1 to 4 carbon atoms;

$R^2$ and $R^4$ are the same or different and each represents a hydrogen atom or an alkyl group having from 1 to 3 carbon atoms;

$R^3$ represents a hydrogen atom or an alkyl group having from 1 to 4 carbon atoms;

$Y^1$ and $Y^2$ are the same or different and each represents a hydrogen atom, an aliphatic acyl group having from 2 to 4 carbon atoms, an unsubstituted aromatic acyl group or a sulfo group; and n is 1 or 2.

13. The compound of claim 1, wherein:

A represents a group of formula (II) or (III), as defined in claim 1:

W represents a methylene group or a group of formula $=C=N-OV$ in which V represents a hydrogen atom, a carboxymethyl group or a 1-carboxy-1-methylethyl group;

U represents a methylene group;

$R^1$ represents a methyl group;

$R^2$ and $R^4$ are the same or different and each represents a hydrogen atom or a methyl group;

$R^3$ represents a methyl or t-butyl group, particularly a methyl group;

$Y^1$ and $Y^2$ are the same and each represents a hydrogen atom or an aliphatic acyl group having from 2 to 4 carbon atoms, particularly a hydrogen atom or an acetyl group; and n is 1.

14. The compound of claim 13, wherein A represents said group of formula (III).

15. The compound of claim 13, wherein W represents a methylene group.

16. The compound of claim 13, wherein W represents a group of formula $=C=N-OH$.

17. The compound of claim 13, wherein $Y^1$ and $Y^2$ are the same and each represents a hydrogen atom or an acetyl group.

18. The compound of claim 13, wherein $R^3$ represents a methyl group.

19. The compound of claim 1, wherein:

A represents a group of formula (III), as defined in claim 1:

W represents a methylene group or a group of formula $=C=N-OH$;

U represents a methylene group;

$R^1$ represents a methyl group;

$R^2$ and $R^4$ are the same or different and each represents a hydrogen atom or a methyl group;

$R^3$ represents a methyl group;

$Y^1$ and $Y^2$ are the same and each represents a hydrogen atom or an acetyl group; and n is 1.

20. The compound of claim 1, selected from the group consisting of 5-{4-[2-hydroxy-2-methyl-4-(3,5,6-trimethyl-1,4-benzoquinon-2-yl)butoxy]benzyl}-2,4-dioxothiazolidine and salts thereof.

21. The compound of claim 1, selected from the group consisting of 5-{4-[4-(2,5-dihydroxy-3,4,6-trimethylphenyl)-2-hydroxy-2-methylbutoxy]benzyl}-2,4-dioxothiazolidine and salts thereof.

22. The compound of claim 1, selected from the group consisting of 5-{4-[4-(2,5-diacetoxy-3,4,6-trimethylphenyl)-2-hydroxy-2-methylbutoxy]benzyl}-2,4-dioxothiazolidine and salts thereof.

23. A pharmaceutical composition for the treatment or prophylaxis of diabetes or hyperlipemia, which comprises an effective amount of an active compound in admixture with a pharmaceutically acceptable carrier or diluent, wherein said active compound is selected from the group consisting of compounds of formula (I), as claimed in claim 1, and pharmaceutically acceptable salts thereof.

24. The composition of claim 23, wherein:

A represents said group of formula (II) or (III);

W represents a methylene group, a carbonyl group or a group of formula $=C=N-OV$ in which V represents a hydrogen atom, an unsubstituted alkyl group having from 1 to 4 carbon atoms or a substituted alkyl group having from 1 to 4 carbon atoms in which the substituents are selected from the group consisting of aryl groups which have from 6 to 10 ring carbon atoms and which are unsubstituted or are substituted by at least one alkyl substituent having from 1 to 5 carbon atoms, carboxy groups and alkoxycarbonyl groups having from 2 to 6 carbon atoms;

U represents a methylene group;

$R^1$ represents a hydrogen atom or an alkyl group having from 1 to 4 carbon atoms;

$R^2$ and $R^4$ are the same or different and each represents a hydrogen atom or an alkyl group having from 1 to 3 carbon atoms;

$R^3$ represents a hydrogen atom or an alkyl group having from 1 to 4 carbon atoms;

$Y^1$ and $Y^2$ are the same or different and each represents a hydrogen atom, an aliphatic acyl group having from 1 to 6 carbon atoms, said aromatic acyl group, or a sulfo group; and n is 1 or 2.

25. The composition of claim 23, wherein:

A represents said group of formula (II) or (III);
W represents a methylene group or a group of formula =C=N—OV
in which V represents a hydrogen atom, an unsubstituted alkyl group having from 1 to 4 carbon atoms or a substituted alkyl group having at least one carboxy substituent;
U represents a methylene group;
$R^1$ represents a hydrogen atom or an alkyl group having from 1 to 4 carbon atoms;
$R^2$ and $R^4$ are the same or different and each represents a hydrogen atom or an alkyl group having from 1 to 3 carbon atoms;
$R^3$ represents a hydrogen atom or an alkyl group having from 1 to 4 carbon atoms;
$Y^1$ and $Y^2$ are the same or different and each represents a hydrogen atom, an aliphatic acyl group having from 2 to 4 carbon atoms, an unsubstituted aromatic acyl group or a sulfo group; and
n is 1 or 2.

26. The composition of claim 23, wherein:
A represents said group of formula (II) or (III);
W represents a methylene group or a group of formula =C=N—OV
in which V represents a hydrogen atom, a carboxymethyl group or a 1-carboxy-1-methylethyl group;
U represents a methylene group;
$R^1$ represents a methyl group;
$R^2$ and $R^4$ are the same or different and each represents a hydrogen atom or a methyl group;
$R^3$ represents a methyl or t-butyl group, particularly a methyl group;
$Y^1$ and $Y^2$ are the same and each represents a hydrogen atom or an aliphatic acyl group having from 2 to 4 carbon atoms, particularly a hydrogen atom or an acetyl group; and
n is 1.

27. The composition of claim 23, wherein:
A represents said group of formula (III);
W represents a methylene group or a group of formula =C=N—OH;
U represents a methylene group;
$R^1$ represents a methyl group;
$R^2$ and $R^4$ are the same or different and each represents a hydrogen atom or a methyl group;
$R^3$ represents a methyl group;
$Y^1$ and $Y^2$ are the same and each represents a hydrogen atom or an acetyl group; and
n is 1.

28. The composition of claim 23, wherein said active compound is selected from the group consisting of:
5-{4-[2-hydroxy-2-methyl-4-(3,5,6-trimethyl-1,4-benzoquinon-2-yl)butoxy]benzyl}-2,4-dioxothiazolidine;
5-{4-[4-(2,5-dihydroxy-3,4,6-trimethylphenyl)-2-hydroxy-2-methylbutoxy]benzyl}-2,4-dioxothiazolidine;
5-{4-[4-(2,5-diacetoxy-3,4,6-trimethylphenyl)-2-hydroxy-2-methylbutoxy]benzyl}-2,4-dioxothiazolidine;
and pharmaceutically acceptable salts thereof.

29. A method for the treatment or prophylaxis of diabetes or hyperlipemia in a mammal, which method comprises administering to said mammal an effective amount of an active compound, wherein said active compound is selected from the group consisting of compounds of formula (I), as claimed in claim 1, and pharmaceutically acceptable salts thereof.

30. The method of claim 29, wherein:
A represents said group of formula (II) or (III);
W represents a methylene group, a carbonyl group or a group of formula =C=N—OV
in which V represents a hydrogen atom, an unsubstituted alkyl group having from 1 to 4 carbon atoms or a substituted alkyl group having from 1 to 4 carbon atoms in which the substituents are selected from the group consisting of aryl groups which have from 6 to 10 ring carbon atoms and which are unsubstituted or are substituted by at least one alkyl substituent having from 1 to 5 carbon atoms, carboxy groups and alkoxycarbonyl groups having from 2 to 6 carbon atoms;
U represents a methylene group;
$R^1$ represents a hydrogen atom or an alkyl group having from 1 to 4 carbon atoms;
$R^2$ and $R^4$ are the same or different and each represents a hydrogen atom or an alkyl group having from 1 to 3 carbon atoms;
$R^3$ represents a hydrogen atom or an alkyl group having from 1 to 4 carbon atoms;
$Y^1$ and $Y^2$ are the same or different and each represents a hydrogen atom, an aliphatic acyl group having from 1 to 6 carbon atoms, said aromatic acyl group, or a sulfo group; and
n is 1 or 2.

31. The method of claim 29, wherein:
A represents said group of formula (II) or (III);
W represents a methylene group or a group of formula =C=N—OV
in which V represents a hydrogen atom, an unsubstituted alkyl group having from 1 to 4 carbon atoms or a substituted alkyl group having at least one carboxy substituent;
U represents a methylene group;
$R^1$ represents a hydrogen atom or an alkyl group having from 1 to 4 carbon atoms;
$R^2$ and $R^4$ are the same or different and each represents a hydrogen atom or an alkyl group having from 1 to 3 carbon atoms;
$R^3$ represents a hydrogen atom or an alkyl group having from 1 to 4 carbon atoms;
$Y^1$ and $Y^2$ are the same or different and each represents a hydrogen atom, an aliphatic acyl group having from 2 to 4 carbon atoms, an unsubstituted aromatic acyl group or a sulfo group; and
n is 1 or 2.

32. The method of claim 29, wherein:
A represents said group of formula (II) or (III);
W represents a methylene group or a group of formula =C=N—OV
in which V represents a hydrogen atom, a carboxymethyl group or a 1-carboxy-1-methylethyl group;
U represents a methylene group;
$R^1$ represents a methyl group;
$R^2$ and $R^4$ are the same or different and each represents a hydrogen atom or a methyl group;
$R^3$ represents a methyl or t-butyl group, particularly a methyl group;
$Y^1$ and $Y^2$ are the same and each represents a hydrogen atom or an aliphatic acyl group having from 2 to 4 carbon atoms, particularly a hydrogen atom or an acetyl group; and
n is 1.

33. The method of claim 29, wherein:
A represents said group of formula (III);

W represents a methylene group or a group of formula =C=N—OH;
U represents a methylene group;
R$^1$ represents a methyl group;
R$^2$ and R$^4$ are the same or different and each represents a hydrogen atom or a methyl group;
R$^3$ represents a methyl group;
Y$^1$ and Y$^2$ are the same and each represents a hydrogen atom or an acetyl group; and
n is 1.

34. The method of claim 29, wherein said active compound is selected from the group consisting of:
5-{4-[2-hydroxy-2-methyl-4-(3,5,6-trimethyl-1,4-benzoquinon-2-yl)butoxy]benzyl}-2,4-dioxothiazolidine;
5-{4-[4-(2,5-dihydroxy-3,4,6-trimethylphenyl)-2-hydroxy-2-methylbutoxy]benzyl}-2,4-dioxothiazolidine;
5-{4-[4-(2,5-diacetoxy-3,4,6-trimethylphenyl)-2-hydroxy-2-methylbutoxy]benzyl}-2,4-dioxothiazolidine;
and pharmaceutically acceptable salts thereof.

* * * * *